United States Patent [19]
Gmeiner

[11] Patent Number: 5,626,567
[45] Date of Patent: May 6, 1997

[54] SYRINGE ASSEMBLY

[76] Inventor: Wilhelm Gmeiner, AM Sudhang 31, 92224 Amberg, Germany

[21] Appl. No.: 493,387

[22] Filed: Jun. 21, 1995

[30] Foreign Application Priority Data

Jun. 21, 1994 [DE] Germany .............. 44 21 617.3
Feb. 3, 1995 [DE] Germany .............. 195 03 474.0

[51] Int. Cl.$^6$ ........................................... A61M 5/00
[52] U.S. Cl. ............................ 604/236; 604/237
[58] Field of Search ...................... 604/232, 236, 604/237, 243, 110, 187, 241, 242, 244, 247; 128/763–765

[56] References Cited

U.S. PATENT DOCUMENTS

| | | | |
|---|---|---|---|
| 3,659,587 | 5/1972 | Baldwin | 604/237 X |
| 3,848,579 | 11/1974 | Villa-Real | 604/237 X |
| 3,874,367 | 4/1975 | Ayres | 604/237 X |
| 3,989,044 | 11/1976 | Meierhoefer | 604/243 X |

Primary Examiner—John D. Yasko
Attorney, Agent, or Firm—Hoffman Wasson & Gitler

[57] ABSTRACT

A needle of an insulin syringe with an exchangeable injection needle and with an insulin ampulla exchangeably connected to the needle is provided and has two coaxial needle portions which are arranged distant from each other. The two needle portions are separated from each other by passage stopping means. The outer needle portion, namely the injection needle, is fastened within a needle supporting body within the needle casing, and the inner needle portion, namely the connecting needle to the insulin ampulla, is arranged within a guide body which is located within the needle casing. The passage stopping means preferably is a flexible membrane or diaphragm with a self-sealing passageway, which acts in such a manner that under pressure a predetermined adjustable amount of insulin fluid is able to pass from one needle portion into the other, and that without pressure action the flexible passage of the membrane locks the flow to the outer needle portion. The membrane is especially provided as a sheet, a thin plate or a foil of rubber or similar flexible material.

5 Claims, 3 Drawing Sheets

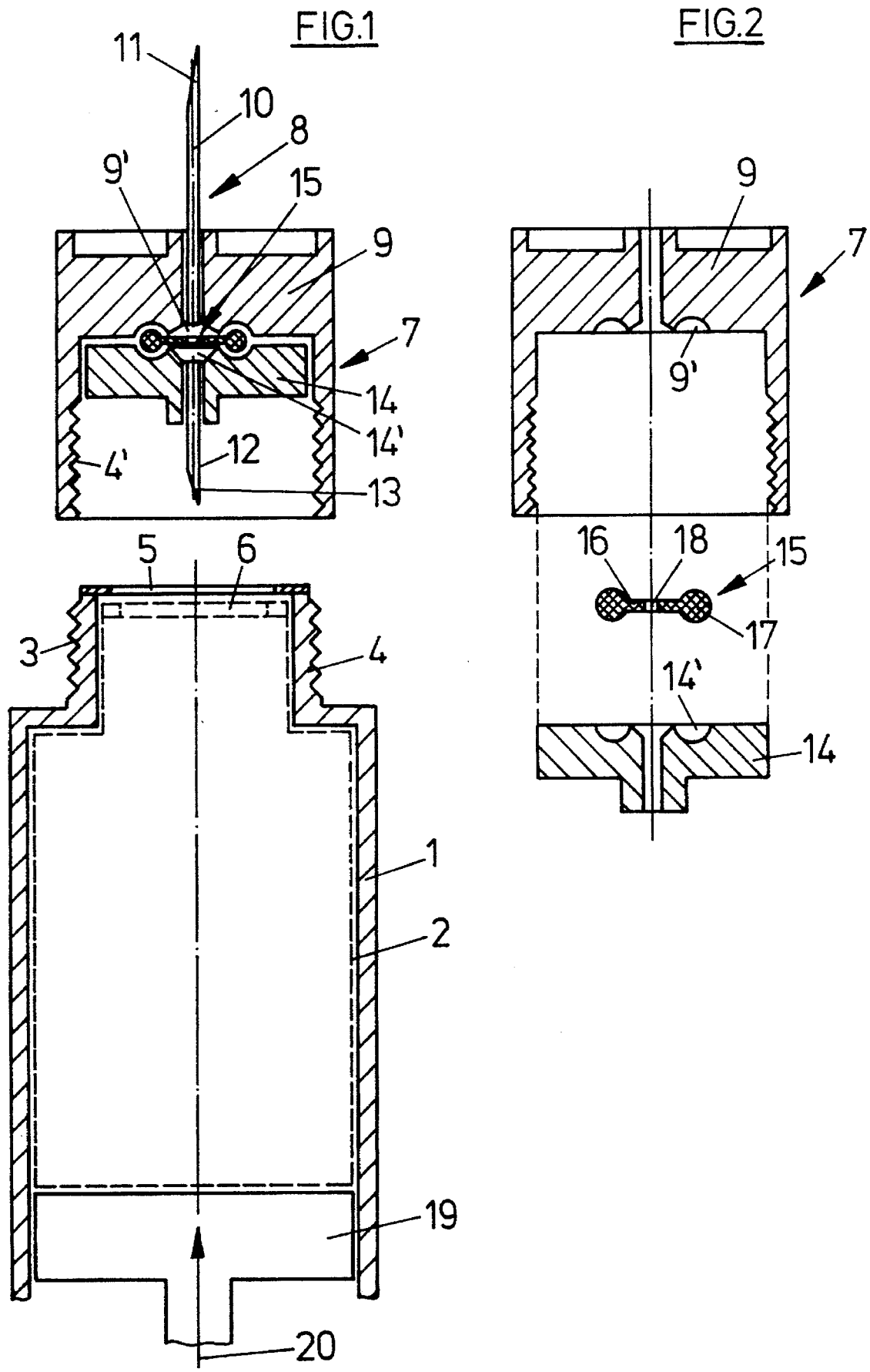

SYRINGE ASSEMBLY

FIELD OF THE INVENTION

This invention relates to an insulin syringe with an exchangeable injection needle and with an insulin ampulla which is arranged within the syringe casing and can releaseably be connected to the needle.

BACKGROUND OF THE INVENTION

For successful treatment and therapy of diabetes it is important for the patient to use an insulin syringe by means of which he (or she) will be able to inject the required amount of insulin himself. This makes it necessary that the user will be able in a most simple and exact manner to inject the required doses of insulin into the body from an insulin ampulla by means of the syringe.

The different insulin syringes on the market which basically operate very similar to each other, have in common that by means of a manually operated piston the insulin included within a container is urged into a needle and is injected into the patient's body via the stitching end of the needle. All known syringes of this type have in common that they are provided with a throughgoing needle and that accordingly there is a continuous connection between the insulin within the container and the outside air via the needle. This has the result that without any operation by the user insulin rather often drops out of the ampulla and that air flows into the ampulla. If subsequent to the injection the finger pressure is removed from the supply piston, the rubber piston within the ampulla releases very slightly rearwardly, whereby air is sucked into the ampulla through the injection needle. Furthermore, if insulin drops out of or evaporates from the ampulla, air flows into the ampulla. This amount of air, which has entered the insulin ampulla is to be removed by the patient before each injection in order to make sure that, in view of the air flown in, failures in doses are avoided by all means if insulin is injected. Removing this air from the insulin ampulla is tiring and time consuming. Rather often elderly people have difficulties in handling the syringe for removing air.

Furthermore, when injecting insulin, blood vessels often will be pierced. The blood exiting from such vessels subsequent to the injection step when removing the pressure from the piston rod and by means of the rubber piston being slightly released rearwardly within the insulin ampulla is sucked into the ampulla through the through-going needle so that the valuable insulin can no longer be used.

SUMMARY OF THE INVENTION

It is an object of the invention to improve the existing insulin syringes in such a manner that an independent undesired exit or evaporation of insulin liquid from the ampulla and as a consequence thereof the entrance of air into the ampulla through the injection needle or the sucking-in of blood into the ampulla is safely prevented and that with each injection the process of ventilation can be dismissed and the adjusted amount of insulin can be injected with an exact dosage at any time.

It is a further object of this invention to provide the forementioned object with extremely simple and effective means in order to be able to manufacture the needle system of insulin syringes in an extremely cheap and effective manner.

According to the subject invention the needle is made of two substantially coaxial needle portions distant from each other, which are separated from each other by passage stopping means, whereby the outer needle portion, namely the injection needle, is fastened within a body of the needle casing, which body holds the needle, and the inner needle portion, which is the connecting needle to the insulin ampulla, is arranged within a guide body fastened within the needle casing. The passage stopping means according to this invention preferably is a flexible membrane (or diaphragm) with a substantially central, flexible, self-sealing passage; the membrane is made of flexible material so that the passage under pressure allows insulin fluid to flow from the insulin ampulla through the inner needle portion into the outer needle portion, if pressure is exerted onto the insulin to be injected, however, without pressurizing the insulin to be injected the flexible passage of the membrane stops the flow of insulin into the outer needle portion and seals it.

According to a special and preferred embodiment of this invention the membrane (or diaphragm) is made of a sheet or foil of rubber or similar flexible material. According to a further embodiment said sheet can be provided with a radially outer, toroidal bead.

Whereas when using a through-going needle there is a continuous connection between the insulin within the ampulla resp. a cartridge, a lumen or the like, and the surrounding air at the needle stitching end, with the subject invention this connection is interrupted by means of a flexible membrane comprising a passage which is closed in the non-actuated condition so that no air resp. no blood can flow into the insulin ampulla.

Because with the device according to the invention in the non-working condition of the syringe the insulin flow from the insulin ampulla to the free end of the tip of the injection needle is interrupted, without actuating the piston, i.e. even by means of shocks, no insulin can discharge through the needle and no air can flow into the ampulla. This ensures that the syringe at any time is ready for exactly dosing and immediately discharging the required insulin dosage which is adjusted by the patient, and that the patient can be sure that no mixture of insulin and air will be injected.

The elastic, flexible membrane which has a substantially central, flexible, self-closing passage (or several passages with equal or different cross-section, in case of a larger amount of insulin involved) is made in such a manner that, if pressure is exerted onto the piston insulin from the ampulla and the inner needle portion passes through the flexible passage, flows into the outer needle section and can be injected into the body through the outer needle.

If the pressure will be released, the passage in view of the flexibility of the material will be closed, if the membrane compresses, and the insulin flow will be sealed or stopped so that no blood nor air can flow into the insulin ampulla. Preferably, the membrane is arranged within a space between the two facing surfaces of the outer and the inner guide bodies, which support one of the two needle sections each, and is provided with a bead, especially of toroidal shape, having a seat within the outer and/or the inner body so that the space receiving the bead is restricted by the two facing surfaces of the two guide bodies and is sealed in such a manner that the membrane has a firm seat. During the state of rest the volume at the membrane facing the ampulla is filled with insulin which cannot flow off through the substantially central passage within the membrane, which passage is closed at rest. If for performing the injection step pressure is exerted onto the piston and thus onto the insulin volume within the ampulla, in view of the exerted pressure insulin passes through the passage and from there through the injection needle into the human body.

The needle system according to the invention comprises the needle casing with the body receiving the injection needle, which body is fixedly connected with the casing, the body receiving the insulin extraction needle which body is inserted into the casing associated to the injection needle body, the stopping device being the membrane between the two bodies, and a syringe casing with an insulin ampulla, which is exchangably received within the casing. Said ampulla, a vial or a cartridge, has a stopper at the output end which stopper is penetrated by the tip of the insulin needle, if the syringe casing with the insulin ampulla is connected, for example screwed onto the needle container. When connecting the syringe casing to the needle casing the insulin delivey needle penetrates the stopper of the insulin ampulla so that insulin can be urged into and through the needle. The body receiving the insulin delivery needle is inserted into the needle casing and is fastened there, for example by being screwed, locked, bonded, welded or the like in such a manner that it is in contact with the needle body and so that both form a volume with each other, which receives the stopping means, such as a membrane, whereby the stopping means is inserted before the insulin delivery needle is positioned. Both bodies can be exchanged so that the inserted body then can be the outer body.

According to a further embodiment of the invention the two facing surfaces of both portions forming the needle body are provided with elevations and recesses which are interengaging each other when being assembled, and a membrane in the form of a flexible foil is arranged between the two body portions so that the projections within the one body portion urge the foil into the mating recess of the other body portion. In this manner the foil is positioned so that a sealing will be obtained.

With a further embodiment of the invention the two body portions forming the needle bodies are not provided with elevations and recesses, but the two facing surfaces are substantially plane. Between both surfaces a membrane, i.e. a flexible foil, is arranged and this foil will be positioned at one of the two facing surfaces, for example by bonding or mechanical clamping, which results in a sealing so that the pressure acting through the one body portion onto the other body portion of the needle body has the result that the foil is fastened. With this embodiment the two facing surfaces of the body portions of the needle body can be roughened, grooved or the like in order to improve the fastening of the foil if glueing of the foil is not wanted. Also with these additional embodiments the foil is provided with a flexible passage which is under pressure so that in the loaded condition insulin will be able to pass through, however, in the unloaded condition no insulin can pass through and the entrance of air or sucking in of blood from outside will be prevented.

The expression "passage" means a way (or several ways) for the insulin through the membrane, which way is dimensioned so that with pressure acting upon the piston an insulin flow will be permitted and insulin will be discharged from the ampulla for being injected, however, which flow will be stopped and the insulin passage in view of the flexibility of the material of the membrane will be prevented if the piston will be released. This passage can be an aperture or penetration (or two or more apertures or penetrations) which is obtained by penetrating the membrane with a needle, or alternatively can be a small, straight or curved slot which under pressure opens sufficiently in order to let insulin pass through, however, which closes automatically and prevents insulin from passing through as soon as the pressure has been released or after the flow of insulin in view of the flexibility of the membrane is stopped. The size of the passage(s) mainly depends on the exerted pressure and on the flexibility of the material which means on the restoring characteristics of the material in order to lock the passage(s) safely when pressure is released. For example, the membrane can be a latex foil which is provided with a tiny or small aperture of the diameter of a needle tip or a needle in order to guaranty a correct operation.

Rather than providing one or several passages in the form of one or several small apertures or perforations within the membrane, i.e. by stitching these perforations with a needle, the material for the membrane already during or after being manufactured can be made in such a manner that at predetermined points the material will be made permeable or porous if pressure is exerted onto the material. For example, the material can be manufactured with varying thicknesses so that there will be spots of reduced thickness through which the insulin can diffuse if it is under pressure.

DETAILED DESCRIPTION OF THE DRAWINGS

In the following the invention will be described in connection with the drawings with various embodiments.

Figure 3:
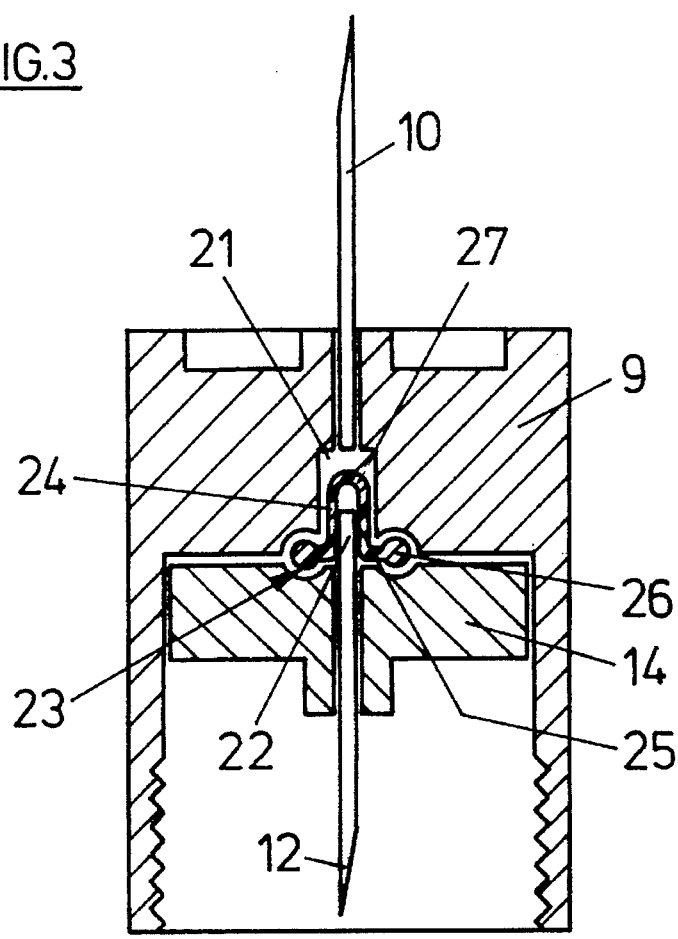
Figure 4:
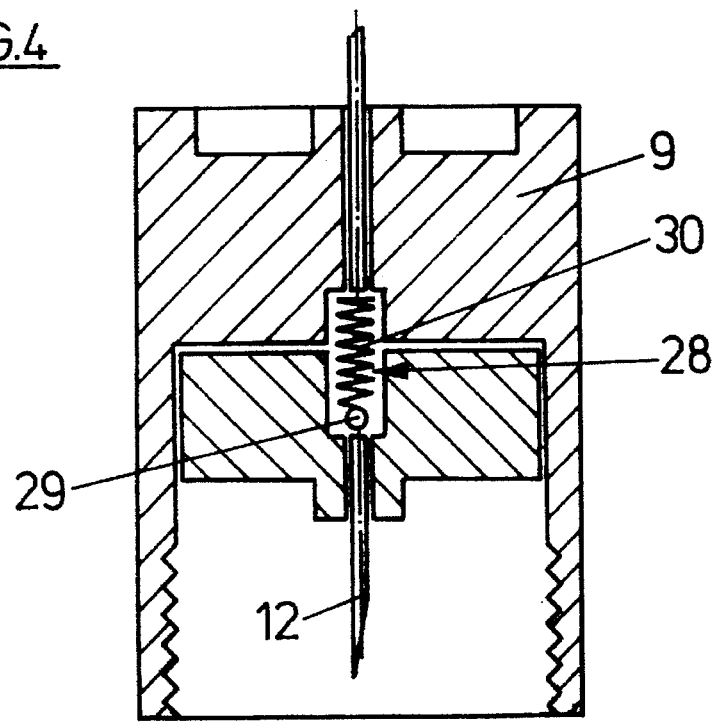
Figure 5:
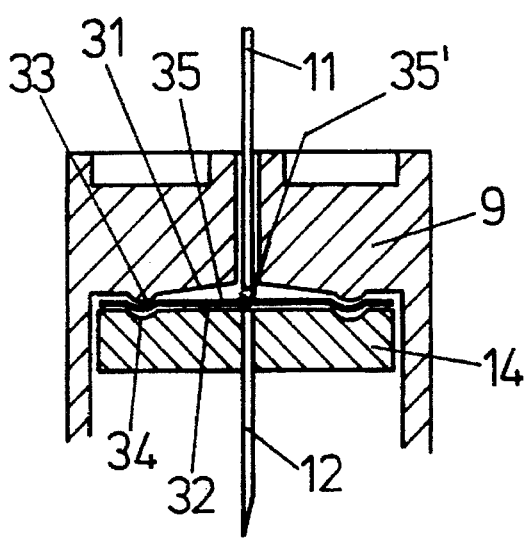
Figure 6:
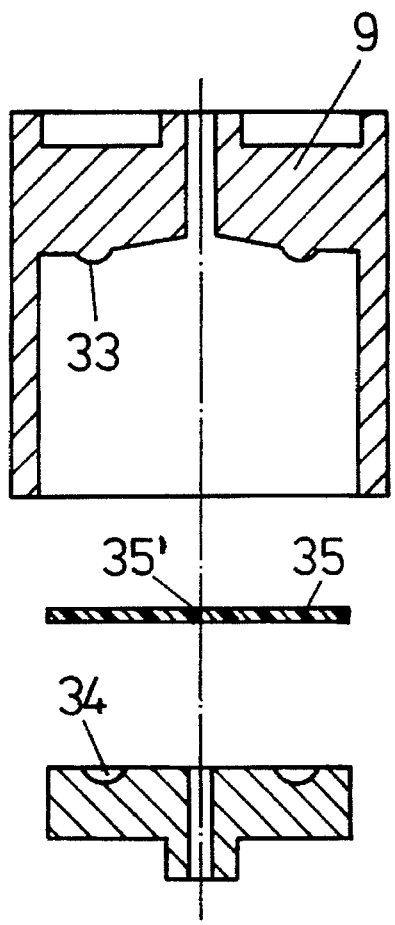
Figure 7:
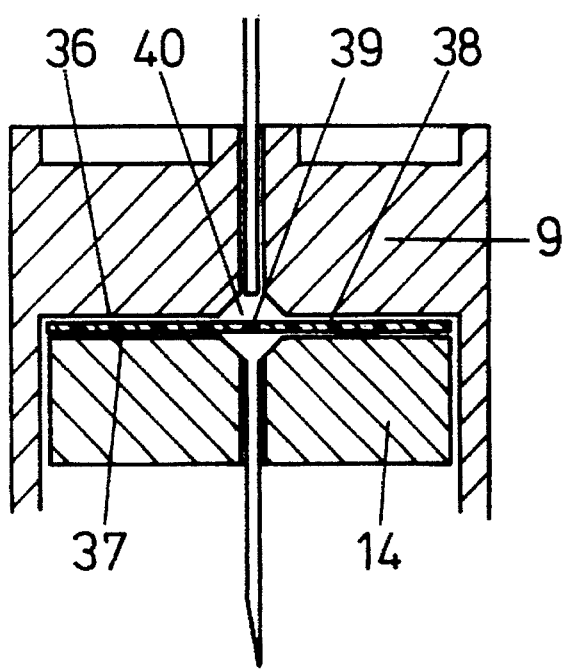
Figure 8:
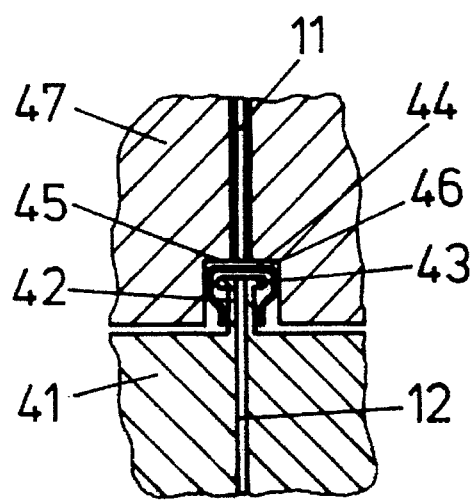

FIG. 1 shows an insulin syringe according to the invention, with needle casing and syringe casing separate from each other, FIG. 2 shows the needle body in an exploded view, FIG. 3 shows a further embodiment of the invention in cross-section, FIG. 4 shows another embodiment of the invention in cross-section, FIG. 5 shows a further embodiment of the invention as a variation of FIG. 1, FIG. 6 shows the embodiment of FIG. 5 in an exploded view, FIG. 7 shows an embodiment, which is a variation of FIG. 5, FIG. 8 shows a variation of the embodiment according to FIG. 3.

DETAILED DESCRIPTION OF THE PREFERRED EMBODIMENTS

The syringe casing 1, which is preferably made of metal or plastic material, receives an insulin container 2, i.e. an insulin ampulla made from glass, the shape of which is adapted to the shape of casing 1. Instead of a glass ampulla 2 an insulin cartridge, i.e. made of plastic, a glass vial or the like can be used. The syringe casing 1 has a neck 3 with an outer thread 4 and an opening 5 which is closed by means of a stopper plate or lid 6, i.e. made of rubber, of plastic foil, or the like, which stopper forms the lid of ampulla 2. The injection needle casing 7 with its thread 4' is screwed onto thread 4 of the syringe casing 1. Said casing 7 comprises the body 9, which receives the outer needle portion 10. The needle system 10, 12 comprises an outer portion 10, which is the injection needle 10 with stitching tip 11, and an inner portion 12, which is the insulin delivery needle with tip 13; the latter is fastened to the inserted body 14, which is fastened to the syringe casing 7 in its inserted position by glueing, clamping, screwing or in any other manner. Bodies 9 and 14 together with their facing surfaces form a free space, into which the inner ends of the two needle portions 10 and 11 extend and in which recesses 9', 14' are formed which are used for receiving flow stopping means 15. Said flow stopping means 15 preferably is a thin, flexible membrane 16, which can be a circular or toroidal bead 17 made from rubber or plastic material. The circular surface of the membrane 16 is provided with a substantially central passage 18 (or two or several passages) which is under pressure in such a manner that by means of a piston 19 working in the direction of arrow 20 acts upon the insulin within the ampulla 2, which pressure propagates through the needle portion 12 onto the membrane and in the loaded condition allows insulin to pass through the passage 18, whereas in the unloaded condition, which is the inactive condition of the membrane, when no pressure is exerted, the passage closes in view of the flexibility of the material of the membrane, so that no air can enter and no insulin can flow out of the syringe.

According to the embodiment of FIG. 3 within body 9 or between the two bodies 9 and 14 a space 21 is provided, into which the inner end 22 of the needle portion 12 extends. A hose-type membrane 23 is slipped over the extending portion 22, and the cap-like portion 24 of the membrane spans around the inner needle end 22. Said cap portion 24 extends radially outwardly into the disc-shaped membrane section 25 and at the radial outer rim turns into the circular or toroidal bead 26. The membrane section 25 can be a circular disc with small cross-section, and the circular bead 26 is provided at a small distance from the cap portion 24 so that a sealed seat of the cap portion 24 is obtained. The cap-shaped membrane portion 24 is provided with a passage (or several passages) facing the inner aperture of the needle portion 12, which passage i.e. is a tiny hole made by means of a needle through which hole in view of the pressure exerted during the injection step insulin can flow into the space 21 and from there into the needle section 10. Instead of providing a membrane with a circular bead the membrane also can be made without any bead if the membrane is fixed between the two bodies in some other manner.

Rather than providing a passage 18 resp. 27, such as a tiny hole within the membrane, which is closed in the inactive position by means of the flexibility of the material, and only allows to let insulin flow through under pressure onto the insulin to be delivered, according to a further embodiment of the invention a small valve, i.e. a ball valve 28 can be provided, which includes a ball 29 and a pressure spring 30 for lifting the ball under the effect of pressure opposite to the action of the spring from the inner end of the needle portion 12 and opens the valve seat. If the pressure onto the piston will be removed spring 30 urges ball 29 against its seat at the needle 12 and prevents the discharge of insulin, the flowing-in of blood (if a blood vessel has been penetrated) or of air into the insulin ampulla. However, this embodiment is more expensive and requires more space so that this is not a preferred solution.

In view of the fact that the needle is divided into two sections which are separated by the membrane, insulin in its resting position cannot flow from the inner needle to the outer needle because the aperture of the membrane resp. the sealing is closed in the resting position. On the other hand, air also cannot flow from the outside through the needle into the insulin ampulla, and no insulin can evaporate.

With the embodiment of FIG. 5 the facing surfaces 31, 32 of the bodies 9 and 14 are formed in such a manner that the surface 31 is provided with a circular, continuous extension 33 and that within surface 32 a corresponding congruent resp. conform recess 34 is provided which forms a circular, continuous recess so that elevations 33 fit into the matching recesses 34. Said recesses and elevations can be provided at the outermost edge of the needle body 14. Of course, the extensions 33 and recesses 34 can be interchanged so that the surface 31 will be provided with recesses and the surface 32 with elevations. Between the two surfaces 31, 32 a flexible sealing diaphragm or foil 35 made of rubber or similar flexible material with passage 35' is provided, which follows the extensions and recesses, if the body 14 is pressed against body 9 so that the foil is fixed over the entire circumference. The stopping means 35 according to FIG. 5 or 6 in the form of a diaphragm or foil which substitutes a membrane 15 with a circular bead according to FIGS. 1–4 is a very simple and useful embodiment of the invention.

According to the embodiment of FIG. 7 the facing surfaces 36, 37 of the bodies 9, 14 are substantially plane, and between the surfaces 36, 37 a membrane 38 in the form of a foil is inserted, which is clamped at the two substantially plane surfaces 36, 37 in the assembled condition of the needle body. Similar to the preceeding figures the membrane according to FIGS. 5 and 7 is provided with one (or several) substantially central passage(s) 39, which corresponds (correspond) with the central passage 18 of FIG. 2. The embodiment of FIG. 7 is an extremely simple embodiment. In order to obtain proper operation mode the membrane can be glued onto one of the surfaces 36, 37 in order to obtain an exact positioning of the membrane and to avoid that the membrane slips away. At both sides of the membrane in the needle area recesses 40 are provided. The membrane 38 is hold plane or is slightly tensioned in order to avoid more extensive displacement of the membrane in the flow direction if insulin flows through. This is also true for the preceeding embodiments.

FIG. 8, which is a variation of the embodiment of FIG. 3, shows that an extension 42, which receives the needle 12, extends only a very little distance upwardly from the body 41, that the extending part 42 is provided with a circular, ring-like extension 43, i.e. a ring-like bead at the upper end or at the cylindrical peripheral wall, that over this extension 43 a membrane or foil 44 is spanned, for example a short length of hose in the form of a cap of rubber, plastic or the like material, which is closed at the upper end and is provided with at least one penetration (the penetration already can be provided at the time of manufacturing by means of a needle or the like) in order to allow insulin to pass through. The membrane or foil closes and seals the aperture 45 of the needle. The free space 46 receiving the preceeding part 42 of the needle and the membrane 44 is enclosed by body 47 preferably in such a manner that the membrane 44 is urged into contact with the ring-like extension 43 by the circular inner wall of body 47, and accordingly, the interior 46 at the lateral portion of the membrane is firmly sealed.

What is claimed is:

1. An insulin syringe with an exchangeable injection needle and an insulin ampulla replaceably connected to said needle and received within a syringe casing, said needle comprising:

two substantially coaxial needle portions, disposed apart from each other, and separated from each other by a flexible foil-type membrane made of a self-sealing elastomeric material and provided with passage stopping means in line with said two coaxial needle portions, an outer injection needle portion being fastened within a needle receiving body of a needle casing, and an inner needle portion for connection to said insulin ampulla, fastened to a guide body positioned within said needle casing, said passage stopping means being formed as one of a tiny slit and a hole, allowing fluid to flow from said insulin ampulla through said inner needle portion to said outer needle portion, when said fluid is pressure actuated, and in absence of pressure said passage stopping means prevents any fluid flow to said outer needle portion, said guide body being inserted into said needle casing by said inner needle portion, and said needle casing having threads, on a cylindrical inner wall, which engage outer threads formed on a neck of said syringe casing so that screwing said syringe casing with said insulin ampulla onto said needle casing causes a tip of said inner needle portion to pierce said insulin ampulla closure and pass insulin to a tip of aid outer needle portion.

2. An insulin syringe according to claim 1, wherein said membrane is made from a sheet of rubber or similar flexible material with a tiny passage hole therein, and an outer peripheral thickening bead.

3. An insulin syringe according to claim 2, wherein said thickening bead is received within said needle receiving body and said guide body forms a seal.

4. An insulin syringe according to claim 1, wherein said needle receiving body and said guide body are provided with central recesses on facing surfaces so that facing ends of said two needle portions extend into chambers at both sides of said membrane.

5. An insulin syringe according to claim 1, wherein said needle receiving body and said guide body form a recess within which said membrane can move at both sides of a plane of said membrane.

* * * * *